United States Patent
Lee

(10) Patent No.: US 9,358,188 B2
(45) Date of Patent: Jun. 7, 2016

(54) WATER-IN-SILICONE OIL MACROEMULSION COSMETIC COMPOSITION

(71) Applicant: SHIN-ETSU CHEMICAL CO., LTD., Tokyo (JP)

(72) Inventor: Taeck-young Lee, Seoul (KR)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 93 days.

(21) Appl. No.: 14/077,833

(22) Filed: Nov. 12, 2013

(65) Prior Publication Data

US 2014/0135406 A1    May 15, 2014

(30) Foreign Application Priority Data

Nov. 13, 2012   (JP) ................. 2012-249315

(51) Int. Cl.
  *A61K 8/06*   (2006.01)
  *A61Q 19/00*  (2006.01)
  (Continued)

(52) U.S. Cl.
  CPC . *A61K 8/064* (2013.01); *A61K 8/20* (2013.01); *A61K 8/23* (2013.01); *A61K 8/34* (2013.01); *A61K 8/345* (2013.01); *A61K 8/365* (2013.01);
  (Continued)

(58) Field of Classification Search
  CPC ........ A51K 8/064; A51K 8/89; A61Q 19/007
  USPC ...................... 514/772.3; 424/455
  See application file for complete search history.

(56) References Cited

U.S. PATENT DOCUMENTS

| 4,150,010 A | 4/1979 | Itoh et al. |
| 4,151,156 A | 4/1979 | Itoh et al. |

(Continued)

FOREIGN PATENT DOCUMENTS

| JP | 55-30741 B2 | 6/1980 |
| JP | 55-39248 B2 | 10/1980 |

(Continued)

OTHER PUBLICATIONS

Dimethicone Copolyol: retrieved from internet: http://cosmeticsinfo.org/ingredient/dimethicone-copolyol. Retrieved on Apr. 2, 2015.*

(Continued)

*Primary Examiner* — Ernst V Arnold
*Assistant Examiner* — Hong Yu
(74) *Attorney, Agent, or Firm* — Birch, Stewart, Kolasch & Birch, LLP

(57) ABSTRACT

A water-in-silicone oil (W/S) macroemulsion cosmetic composition of waterdrop quick break type is provided. The silicone oil phase part (S) contains a partly crosslinked emulsifiable silicone elastomer, a partly crosslinked non-emulsifiable silicone elastomer, and silicone oil, and the aqueous phase part (W) contains 1,3-butylene glycol and a lower alcohol, and also, at least one member selected from the group consisting of organic acid salts, inorganic salts, and polyhydric alcohols excluding glycerin and 1,3-butylene glycol as a freeze stabilizer at a predetermined composition. The cosmetic composition instantaneously releases water upon application on the skin. The cosmetic composition is stable at the extremely low temperature of −20° C., and it retains its dispersion stability even after repeated freezing and thawing, and accordingly, it can be used in a variety of cosmetic product.

9 Claims, 2 Drawing Sheets

(51) Int. Cl.
- *A61K 8/89* (2006.01)
- *A61K 8/34* (2006.01)
- *A61K 8/365* (2006.01)
- *A61K 8/60* (2006.01)
- *A61K 8/86* (2006.01)
- *A61K 8/891* (2006.01)
- *A61K 8/894* (2006.01)
- *A61K 8/895* (2006.01)
- *A61K 8/20* (2006.01)
- *A61K 8/23* (2006.01)

(52) U.S. Cl.
CPC ... *A61K 8/60* (2013.01); *A61K 8/86* (2013.01); *A61K 8/89* (2013.01); *A61K 8/891* (2013.01); *A61K 8/894* (2013.01); *A61K 8/895* (2013.01); *A61Q 19/00* (2013.01); *A61Q 19/007* (2013.01); *A61K 2800/5922* (2013.01)

(56) References Cited

U.S. PATENT DOCUMENTS

| | | | |
|---|---|---|---|
| 4,201,698 | A | 5/1980 | Itoh et al. |
| 4,376,184 | A | 3/1983 | Itoh et al. |
| 5,599,533 | A * | 2/1997 | Stepniewski et al. ...... 424/78.02 |
| 5,811,487 | A * | 9/1998 | Schulz et al. ................. 524/862 |
| 5,876,702 | A * | 3/1999 | Gers-Barlag et al. ........... 424/59 |
| 6,379,682 | B1 * | 4/2002 | Tchinnis et al. .............. 424/401 |
| 7,923,585 | B2 | 4/2011 | Ishida et al. |
| 8,105,617 | B2 | 1/2012 | Polonka et al. |
| 2002/0197228 | A1 * | 12/2002 | LaSala et al. .............. 424/70.12 |
| 2009/0252774 | A1 | 10/2009 | Kamei et al. |
| 2011/0028571 | A1 | 2/2011 | Hayakawa |
| 2011/0301247 | A1 | 12/2011 | Hayakawa et al. |
| 2012/0237461 | A1 | 9/2012 | Yu et al. |

FOREIGN PATENT DOCUMENTS

| | | |
|---|---|---|
| JP | 55-39261 B2 | 10/1980 |
| JP | 57-17011 B2 | 4/1982 |
| JP | 58-13093 B2 | 3/1983 |
| JP | 2002-293975 A | 10/2002 |
| JP | 4949680 B2 | 6/2012 |
| KR | 10-1070819 B1 | 9/2011 |
| KR | 10-1084875 B1 | 11/2011 |
| KR | 10-1158281 B1 | 6/2012 |
| WO | WO 2009/103602 A1 | 8/2009 |

OTHER PUBLICATIONS

Tekmar RW 20 DZM Overhead Stirrer: retirieved from internet: http://www.hitechtradercom/Laboratory%20Equipment/Mixing/Overhead%20Stirrer/Tekmar-RW-20-DZM-Overhead-Stirrer/001140812/88267/88267-p.aspx. Retrieved on Apr. 2, 2015.*
Extended European Search Report dated Aug. 28, 2015, for European Application No. 13192767.5.

* cited by examiner

WATER-IN-SILICONE OIL MACROEMULSION COSMETIC COMPOSITION

CROSS-REFERENCE TO RELATED APPLICATION

This non-provisional application claims priority under 35 U.S.C. §119(a) on Patent Application No. 2012-249315 filed in Japan on Nov. 13, 2012, the entire contents of which are hereby incorporated by reference.

TECHNICAL FIELD

This invention relates to a water-in-silicone oil (W/S) macroemulsion cosmetic composition of waterdrop quick break type wherein the emulsion breaks instantaneously with the application of the cosmetic composition on the skin thereby releasing the water content.

BACKGROUND ART

Cosmetic products are produced by using various emulsion systems (emulsion compositions) such as oil in water (O/W) emulsion, water in oil (W/O) emulsion, and water-in-silicone oil (W/S) emulsion to convey various components.

Cosmetic composition for skin care is directly applied to the skin, and therefore, the demands for such composition include not only the functionality but also good skin feeling. Recently, there is a growing interest for a sensuous cosmetic product which is capable of providing unique feeling during or after the use of the composition by the change of the emulsion system (emulsion composition) or the composition of the system.

An example is cool feel cosmetic composition having a menthol derivative added in the cosmetic composition (for example, Patent Document 1: Korean Patent No. 10-1084875). Another example is a cosmetic composition comprising a cationic copolymer containing monomer unit selected from acryloylethyltri($C_1$-$C_3$ alkyl) ammonium salts and a mica having a carbon dioxide coating, and this cosmetic composition realizes a smooth skin by soft focus effect. (See for example, Patent Document 2: WO 2009/103602.)

Another type of products that are in focus is waterdrop quick break type products which intensively supply water component to the skin simultaneously with the application of the product to the skin by bursting of the waterdroplets.

Also disclosed is a cosmetic product providing the skin with a moist feeling like that of the lotion as well as cool feeling and humectant feeling, and which has also realized excellent make up effects and stability. This composition is prepared by mixing PEG/PPG-19/19 dimethicone or lauryl PEG-9 polydimethylsiloxyethyl dimethicone with the oil phase of the water-in-oil emulsion composition, and when applied to the skin, the interior aqueous phase is instantaneously released simultaneously with the breakage of the emulsion of the water-in-oil foundation emulsion. (See for example, Patent Document 3: Korean Patent No. 10-1158281.)

Water-in-silicone and silicone-in-water emulsion compositions having excellent waterdrop quick break effect, cosmetic retention, skin adhesion, and skin feeling are also proposed. The emulsion composition comprises a polyionic complex of an anionic hydrophilic macromolecule substance bonded with a hydrophobic cationic monomer by ionic bond, a silicone based crosspolymer, and a silicone oil. (See for example, Patent Document 4: Korean Patent No. 10-1070819.)

As disclosed in the Patent Document 3, the emulsion composition should be highly stable at various temperatures if the emulsion composition is to be used in a cosmetic product.

Stability of the cosmetic composition is generally evaluated in a cyclic evaluation by observing the dispersion state of the emulsion at different temperatures (high temperature, low temperature, and room temperature) and in different atmospheres. Patent Document 3 discloses an observation of the dispersion state by repeating the incremental 1 month cycle of 45° C.→room temperature→5° C. In this case, the observation is conducted by occasionally changing the temperature and time depending on the dosage form of the cosmetic product.

The use of 5° C. for the "low" temperature may be adequate in the case of the indoor use. The cosmetic product, however, may be exposed to a lower temperature in the delivery and storage of the cosmetic product, and also, in the use of the product in colder district, and at a temperature lower than 5° C., there is a risk that the emulsion is destroyed inviting separation of the aqueous phase part and the oil phase part.

Accordingly, the product is also tested by a freeze test at a temperature of lower than −20° C., and also, by a repeated freeze-thaw stability test cycles as a preparation for shipping to cold district.

CITATION LIST

Patent Document 1: Korean Patent No. 10-1084875
Patent Document 2: WO 2009/103602
Patent Document 3: Korean Patent No. 10-1158281
Patent Document 4: Korean Patent No. 10-1070819

SUMMARY OF INVENTION

Technical Problem

An object of the present invention is to provide a water-in-silicone oil (W/S) macroemulsion cosmetic composition which can be produced into a waterdrop quick break type product which intensively supply water component to the skin simultaneously with the application of the product to the skin by bursting of the waterdrops, and which is capable of retaining its stability in repeated freeze-thaw cycles.

Solution to Problem

The inventors of the present invention made an intensive study to realize the object as described above, and found that a waterdrop quick break-type preparation can be produced by using a constitution comprising a silicone oil phase part (S) comprising a partly crosslinked emulsifiable silicone elastomer, a partly crosslinked non-emulsifiable silicone elastomer, a non-crosslinked silicone emulsifier, and a silicone oil, and an aqueous phase part (W) substantially free from glycerin comprising 1,3-butylene glycol and a lower alcohol at a total amount of 13 to 18% by weight of the entire composition, and at least one member selected from the group consisting of organic acid salts, inorganic salts, and polyhydric alcohols other than glycerin and 1,3-butylene glycol at a total amount of 0.4 to 3.0% by weight of the entire composition in water as a freeze stabilizer. The inventors also found that a water-in-silicone oil macroemulsion cosmetic product having an improved freeze and thaw stability can be obtained by using such constitution. The present invention has been completed on the bases of such finding.

Accordingly, the present invention provides a water-in-silicone oil (W/S) macroemulsion cosmetic composition comprising a silicone oil phase part (S) and an aqueous phase part (W) as described below.

[1] A water-in-silicone oil macroemulsion cosmetic composition comprising a silicone oil phase part and aqueous phase, wherein the silicone oil phase part (S) comprises a partly crosslinked emulsifiable silicone elastomer, a partly crosslinked non-emulsifiable silicone elastomer, a non-crosslinked silicone emulsifier, and a silicone oil, and the aqueous phase part is substantially free from glycerin, and the aqueous phase part (W) contains in water 1,3-butylene glycol and a lower alcohol at a total amount of 13 to 18% by weight of the entire composition, and at least one member selected from the group consisting of organic acid salts, inorganic salts, and polyhydric alcohols other than glycerin and 1,3-butylene glycol at a total amount of 0.4 to 3.0% by weight of the entire composition as a freeze stabilizer.

[2] A water-in-silicone oil macroemulsion cosmetic composition of [1] wherein the 1,3-butylene glycol and the lower alcohol is 4:1 to 1:2 in the weight ratio.

[3] A water-in-silicone oil macroemulsion cosmetic composition of [1] or [2] wherein the content of the organic acid salt is present in an amount of 0.05 to 0.5% by weight of the entire composition.

[4] A water-in-silicone oil macroemulsion cosmetic composition according to any one of [1] to [3] wherein the lower alcohol is at least one member selected from methanol, ethanol, isopropanol, butanol, and pentanol.

[5] A water-in-silicone oil macroemulsion cosmetic composition according to any one of [1] to [4] wherein the organic acid salt is at least one member selected from the group consisting of sodium citrate, sodium formate, sodium acetate, and potassium acetate.

[6] A water-in-silicone oil macroemulsion cosmetic composition according to any one of [1] to [5] wherein the inorganic salt is at least one member selected from sodium chloride, potassium chloride, calcium chloride, magnesium chloride, and magnesium sulfate.

[7] A water-in-silicone oil macroemulsion cosmetic composition according to [6] wherein the inorganic salt is at least one member selected from sodium chloride and potassium chloride.

[8] A water-in-silicone oil macroemulsion cosmetic composition according to any one of [1] to [7] wherein the polyhydric alcohol is least one member selected from ethylene glycol, propylene glycol, dipropylene glycol, tripropylene glycol, diethylene glycol, sorbitol, mannitol, maltitol, lactitol, glucose, polyethylene glycol, and polypropylene glycol.

Advantageous Effects of Invention

The water-in-silicone oil (W/S) macroemulsion cosmetic composition of the present invention will attract users since it has enabled visual confirmation of the water supply to the skin by instantaneous water release. The water-in-silicone oil macroemulsion cosmetic composition of the present invention is also stable at an extremely low temperature of −20° C., and the cosmetic composition is capable of retaining the stable dispersed condition after repeated freeze and thaw cycles. Accordingly, the cosmetic composition can be used in various cosmetic product.

DESCRIPTION OF EMBODIMENTS

Figure 1:
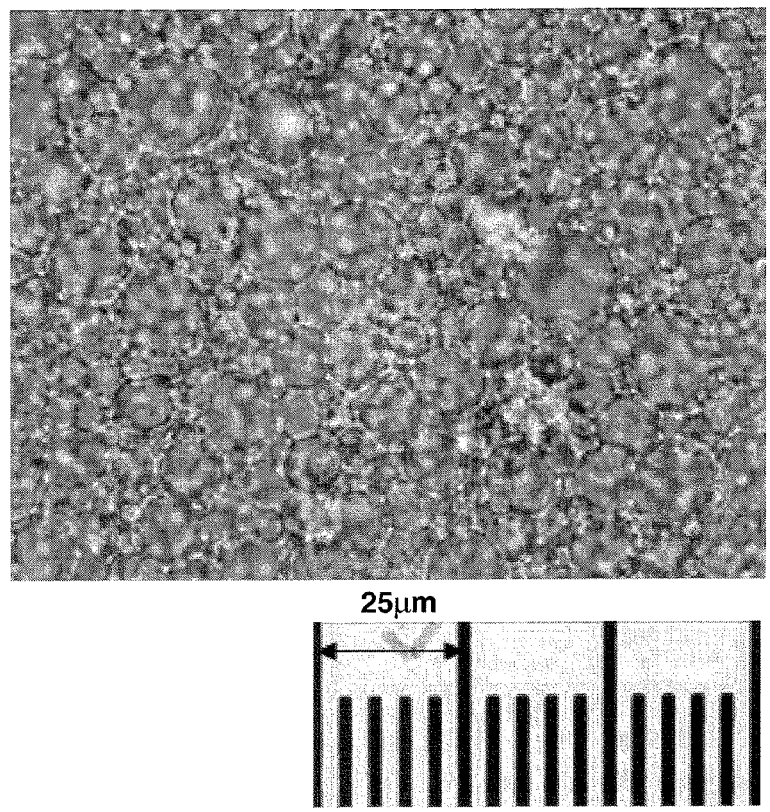
FIG. 1 is a picture taken by an optical microscope of the particles of the water-in-silicone oil (W/S) macroemulsion produced in Example 2.
Figure 2A:
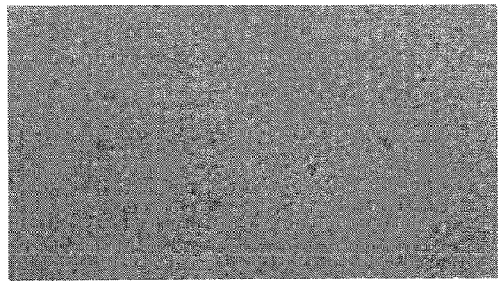
FIG. 2(a) to 2(g) are respectively pictures taken by an optical microscope of the water-in-silicone oil (W/S) macroemulsions produced in Examples 1, 2, 3, 4, 6, 7, and 8.
Figure 2B:
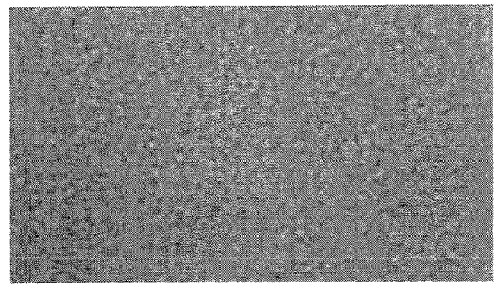
Figure 2C:
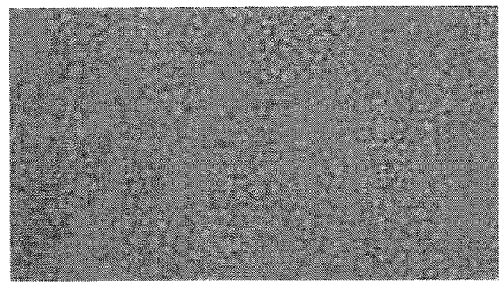
Figure 2D:
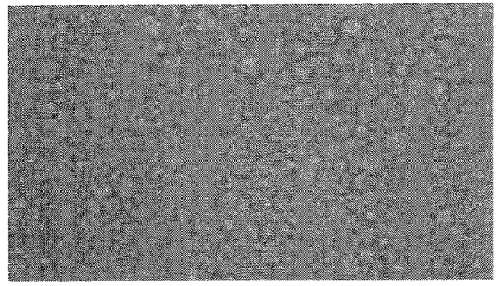
Figure 2E:
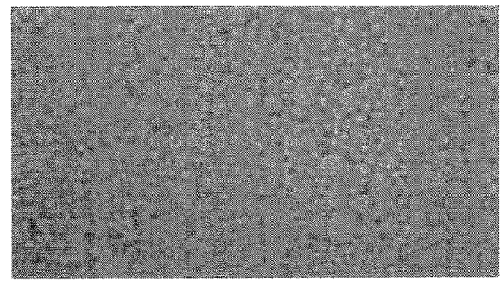
Figure 2F:
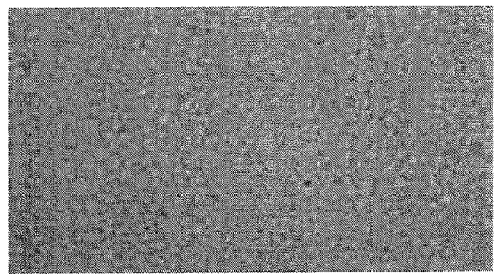
Figure 2G:
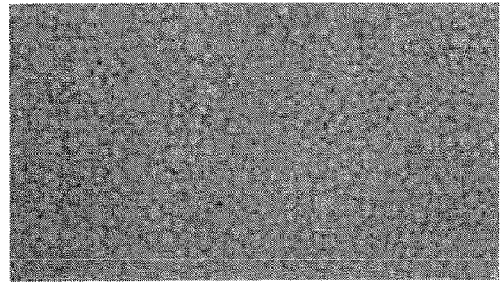

Next, the present invention is described in detail.

The present invention provides a water-in-silicone oil (W/S) macroemulsion cosmetic composition which can be applied for a cosmetic product of waterdrop quick break-type which instantaneously releases water upon its application on the skin by the breakage of the emulsion. The water-in-silicone oil (W/S) macroemulsion cosmetic composition comprises the aqueous phase part (W) and the silicone oil phase part (S), and the aqueous phase part (W) contains a freeze stabilizer in the water to thereby enable retention of the stable dispersion phase after repeated freeze and thaw cycles.

The freeze stabilizer which is substantially free from glycerin contains 1,3-butylene glycol and a lower alcohol, and also, at least one member selected from the group consisting of organic acid salts, inorganic salts, and polyhydric alcohols other than glycerin and 1,3 butylene glycol at a limited content in relation to the entire composition. The reliable low temperature stability of the cosmetic composition is thereby realized.

The freeze stabilizer contains 1,3-butylene glycol and a lower alcohol at a total content of 13 to 18% by weight of the entire amount of the composition. The content below such range may invite phase separation in the repeated cycles of freezing and thawing or during the storage at an extremely low temperature of −20° C. The content beyond such range may be economically disadvantageous in view of the slight improvement in the advantageous effects, and therefore, the content is preferably in the range as described above.

In this case, the ratio of the 1,3-butylene glycol and the lower alcohol is preferably 4:1 to 1:2, and more preferably 3:2 to 4:5 in the weight ratio of the 1,3-butylene glycol:lower alcohol. When the use of the 1,3-butylene glycol is insufficient, the composition may suffer from the problem of loss of the moist feeling, while excessive use of the 3-butylene glycol may invite problems of poor spreadability and thickened feeling.

The lower alcohol may be a monohydric alcohol containing 1 to 5 carbon atoms, and one or more of methanol, ethanol, isopropanol, butanol, and pentanol may be used. Such lower alcohol may function as an agent for lowering the freezing point of the emulsion, and as a consequence, the freeze-thaw stability is improved.

In the meanwhile, the organic acid salt used may be one or more of sodium citrate, sodium formate, sodium acetate, and potassium acetate. This component also lowers the freezing point of the emulsion, and the stability for repeated freeze-thaw cycles is thereby improved.

The inorganic salt used may be one or more of a monovalent salt selected from the group consisting of sodium chloride, potassium chloride, and combinations thereof or a divalent salt selected from the group consisting of calcium chloride, magnesium chloride, magnesium sulfate, and combinations thereof. This component also lowers the freezing point of the emulsion, and the stability for repeated freeze-thaw cycles is thereby improved.

The polyhydric alcohol used may be one or more of ethylene glycol, propylene glycol, dipropylene glycol, tripropylene glycol, diethylene glycol, sorbitol, mannitol, maltitol, lactitol, glucose, polyethylene glycol, and polypropylene glycol. Use of the polyethylene glycol and the polypropylene glycol having a molecular weight of 500 to 20,000 is advantageous in view of the low temperature stability. In the present invention, the molecular weight may be determined as a number average molecular weight in a gel permeation chromatography (GPC) typically conducted by using tetrahydrofuran (THF) or toluene for the development solvent.

The component selected from the organic acid salt, the inorganic salt, and the polyhydric alcohol may be used alone or in combination of two or more. The total content of such component, however, is in the range of 0.4 to 3.0% by weight of the entire composition. Insufficient content may result in the failure of obtaining the stable composition while excessive content may result the loss of stability and thickened feeling.

The component selected from the organic acid salt, the inorganic salt, and the polyhydric alcohol is most preferably an organic acid salt such as sodium citrate, and such organic acid salt may be used in combination with an inorganic salt and/or a polyhydric alcohol. In such a case, the content of the organic acid salt is typically in the range of approximately 0.05 to 0.5% by weight of the entire composition.

Use of the freeze stabilizer substantially free from glycerin containing 1,3-butylene glycol and a lower alcohol, and also, at least one member selected from the group consisting of organic acid salt, inorganic salt, and polyhydric alcohol other than glycerin and 1,3 butylene glycol in the aqueous phase part enables production of a water-in-silicone oil (W/S) macroemulsion composition with reliable stability after repeated freezing and thawing.

The freeze stabilizer may be used in various emulsion compositions, and preferably, the freeze stabilizer is used in an emulsion cosmetic composition for producing the cosmetic product of waterdrop quick break type described in the present invention which instantaneously releases the water content by breakage of the emulsion when the cosmetic product is applied to the skin.

The aqueous phase part (W) contains 1,3-butylene glycol and lower alcohol, and also, at least one member selected from polyhydric alcohols other than the glycerin and the 1,3-butylene glycol at a limited content as the freeze stabilizer as described above together with the water.

The water used in the aqueous phase part is preferably purified water.

The emulsion cosmetic composition according to the present invention is a water-in-silicone oil (W/S) emulsion comprising an aqueous phase part (W) and a silicone oil phase part (S) mainly comprising a silicone oil agent. It is to be noted that the silicone oil phase part (S) may contain a non-silicone hydrocarbon oil agent at a content of typically up to 50% by weight in relation to the entire silicone oil phase part (S).

The silicone oil phase part (S) mainly comprising a silicone oil agent may further comprise a partly crosslinked emulsifiable silicone elastomer, a partly crosslinked non-emulsifiable silicone elastomer, and a non-crosslinked silicone emulsifier, and also, commonly used additives (for example, non-silicone hydrocarbon oil agent) in the silicone oil.

The silicone oil in the silicone oil phase part (S) is not particularly limited in the present invention as long as it is a non-crosslinked and non-reactive silicone oil, and any known silicone oils may be used. Examples include dimethicone, diphenyl dimethicone, diphenylsiloxyphenyl trimethicone, a mixture of dimethicone and cyclopentasiloxane, and cyclopentasiloxane.

Exemplary non-limiting commercially available silicone oils include KF-96 series, KF-53, KF-54, KF-56A, KF-9008, KF-9011, KF-9014, X-21-5495, KF-9028, KF-995, and the like manufactured by Shin-Etsu Chemical Co., Ltd., and the preferred is dimethicone (KF-96A-6cs).

The silicone oil is typically incorporated at an amount of approximately 25 to 85% by weight in relation to the total weight of the silicone oil phase part (S).

The partly crosslinked emulsifiable silicone elastomer is not particularly limited in the present invention, and any silicone oil known in the art may be used. Examples include a mixture of dimethicone/PEG-10/15 crosspolymer and dimethicone, a mixture of dimethicone/PEG-10/15 crosspolymer and cyclopentasiloxane, a mixture of PEG-15/lauryl dimethicone crosspolymer and a mineral oil, a mixture of PEG-15/lauryl dimethicone crosspolymer and isododecane, a mixture of PEG-15/lauryl dimethicone crosspolymer and triethylhexanoi, a mixture of PEG-10/lauryl dimethicone crosspolymer and PEG-15/lauryl dimethicone crosspolymer and squalane, a mixture of PEG-15/lauryl polydimethylsiloxyethyl dimethicone crosspolymer and isododecane, a mixture of PEG-15/lauryl polydimethylsiloxyethyl dimethicone crosspolymer and cyclopentasiloxane, a mixture of dimethicone/polyglycerin-3 crosspolymer and dimethicone, a mixture of lauryl dimethicone/polyglycerin-3 crosspolymer and a mineral oil, a mixture of lauryl dimethicone/polyglycerin-3 crosspolymer and isododecane, a mixture of lauryl dimethicone/polyglycerin-3 crosspolymer and triethylhexanoin, a mixture of lauryl dimethicone/polyglycerin-3 crosspolymer and squalane, a mixture of polyglycerin-3/laurylpolydimethylsiloxyethyl dimethicone crosspolymer and isododecane, and a mixture of polyglycerin-3/laurylpolydimethylsiloxyethyl dimethicone crosspolymer and cyclopentasiloxane.

Exemplary non-limiting commercially available partly crosslinked emulsifiable silicone elastomers include KSG-210, KSG-240, KSG-310, KSG-320, KSG-330, KSG-340, KSG-320Z, KSG-350Z, KSG-710, KSG-810, KSG-820, KSG-830, KSG-840, KSG-820Z, KSG-850Z, and the like manufactured by Shin-Etsu Chemical Co., Ltd., and the preferred is KSG-210 (a mixture of dimethicone/PEG-10/15 crosspolymer and dimethicone).

The partly crosslinked emulsifiable silicone elastomer is typically incorporated at an amount of approximately 3 to 50% by weight in relation to the total weight of the silicone oil phase part (S).

The partly crosslinked non-emulsifiable silicone elastomer is not particularly limited in the present invention, and any silicone oil known in the art may be used. An example is a mixture of a silicone crosspolymer and at least one hydrocarbon oil and/or one silicone oil.

Examples include a mixture of dimethicone/vinyl dimethicone crosspolymer and cyclopentasiloxane, a mixture of dimethicone/vinyl dimethicone crosspolymer and dimethicone, a mixture of dimethicone/vinyl dimethicone crosspolymer and methyl triethicone, a mixture of dimethicone/vinyl dimethicone crosspolymer and isododecane, a mixture of dimethicone/phenylvinyl dimethicone crosspolymer and diphenylethylsiloxyphenyl trimethicone, a mixture of vinyl dimethicone/lauryl dimethicone crosspolymer and a mineral oil, a mixture of vinyl dimethicone/lauryl dimethicone crosspolymer and isododecane, a mixture of vinyl dimethicone/lauryl dimethicone crosspolymer and triethylhexanoin, a mixture of vinyl dimethicone/lauryl dimethicone crosspolymer and squalane, a mixture of laurylpolydimethylsiloxyethyl dimethicone/bis-vinyl dimethicone crosspolymer and isododecane, and a mixture of laurylpolydimethylsiloxy ethyl dimethicone/bis-vinyl dimethicone crosspolymer and cyclopentasiloxane.

Exemplary non-limiting commercially available partly crosslinked non-emulsifiable silicone elastomers include KSG-15, KSG-16, KSG-1610, KSG-106, KSG-18A, KSG-41, KSG-42, KSG-43, KSG-44, KSG-042Z, KSG-045Z, and the like manufactured by Shin-Etsu Chemical Co., Ltd., and the preferred is KSG-15 (a mixture of dimethicone/vinyl dimethicone crosspolymer and cyclopentasiloxane).

The partly crosslinked non-emulsifiable silicone elastomer is typically incorporated at an amount of approximately 2 to 50% by weight in relation to the total weight of the silicone oil phase part (S).

It is to be noted that the silicone oil, the partly crosslinked emulsifiable silicone elastomer, and the partly crosslinked non-emulsifiable silicone elastomer may be used so that the partly crosslinked emulsifiable silicone elastomer is typically at 0.05 to 1.5 parts by weight, and the partly crosslinked non-emulsifiable silicone elastomer is typically at 0.025 to 1.5 parts by weight in relation to 1 part by weight of the silicone oil.

The non-crosslinked silicone emulsifier is not particularly limited in the present invention, and any silicone oil known in the art may be used. Examples in clued polyether modified silicone or polyglycerin modified silicone such as PEG-3 dimethicone, PEG-10 dimethicone, PEG-9 methyl ether dimethicone, PEG-9 polydimethylsiloxyethyl dimethicone, lauryl PEG-9 polydimethylsiloxyethyl dimethicone, polyglyceryl-3 polydimethylsiloxyethyl dimethicone, and lauryl polyglyceryl-3 polydimethylsiloxyethyl dimethicone.

Exemplary non-limiting commercially available non-crosslinked silicone emulsifiers include KF-6015, KF-6016, KF-6017, KF-6028, KF-6038, KF-6104, KF-6105, and the like manufactured by Shin-Etsu Chemical Co., Ltd., and the preferred is KF-6017 (PEG-10 dimethicone).

The non-crosslinked silicone emulsifier is typically incorporated at an amount of approximately 0.03 to 11.5% by weight in relation to the total weight of the silicone oil phase part (S).

It is to be noted that, in the present invention, all of the silicone oil, the partly crosslinked emulsifiable silicone elastomer, the partly crosslinked non-emulsifiable silicone elastomer, and the non-crosslinked silicone emulsifier are preferably those having a cone penetration (worked penetration) at 25° C. of approximately 300 to 450, and in particular, approximately 330 to 430. The cone penetration (worked penetration) may be measured in accordance with JIS K2220.

The production of the water-in-silicone oil (W/S) macro-emulsion cosmetic composition of the present invention may be accomplished by applying the production schemes commonly used for the production of cosmetic compositions.

If desired, the cosmetic composition may also contain water soluble physiologically active component, oil soluble physiologically active component, solvent, additive, or the like which is known in the art. The solvent is the one used for dissolving the oil-soluble components, and a solvent such as ethanol may be used for this purpose.

Exemplary additives include humectant, fatty acid, antiseptic, pH adjusting agent, antioxidant, UV filter, pigment, dye, flavor, stabilizer, and thickener, which may be adequately selected by those skilled in the art.

The humectant may be one member selected from the group consisting of amino acid, sodium lactate, sodium pyrrolidonecarboxylate, xyloglucan, quince seed, carageenan, pectin, mannan, curdlan, galactan, dermatan sulfate, glycogen, keratan sulfate, chondroitin, mucoitinsulfuric acid, keratosulfate, locust bean gum, succinoglycan, calonym acid, hyaluronic acid, heparin sulfate, sodium hyaluronate, collagen, mucopolysaccharide, chondroitin sulfate, dimethylpolysiloxane, methylphenylsiloxane, supernatant of *lactobacillus* or *Bifidobacterium*, and mixtures thereof.

Exemplary fatty acids include hydrocarbon and one fatty acid selected from the group consisting of lauric acid, myristic acid, palmitic acid, stearic acid, oleic acid, linolenic acid, and mixtures thereof.

The thickener is used for the purpose of providing adequate viscosity with the cosmetic composition during its use to thereby improve feeling of the use. The thickener may be one member selected from the group consisting of sodium alginate, xanthan gum, aluminum silicate, quince seed extract, gum arabic, hydroxyethyl guar gum, carboxymethyl guar gum, guar gum, dextran, tragacanth gum, cellulose, hydroxypropyl cellulose, methyl hydroxypropyl cellulose, methylcellulose, carboxymethylcellulose, hydroxyethylcellulose, carboxyvinyl polymer, polyvinyl alcohol, polyvinylpyrrolidone, and combinations thereof. Preferably, the thickener used is a carbomer which is capable functioning as a thickener at a wide range of pH even and at a thin concentration, with the transparency retained.

The lipid used may be one member selected from the group consisting of mango butter, shea butter, cocoa seed butter, macadamia nut oil, batyl alcohol, behenyl alcohol, cetostearyl alcohol, cetyl alcohol, stearyl alcohol, and combinations thereof.

Examples of the antiseptic used include benzoate salt, salicylate salt, sorbate salt, dihydroactate salt, paraoxybenzoate ester, 2,4,4-trichloro-2-hydroxydiphenyl ether, 3,3,4-trichlorocarbanilide, benzalkonium chloride, hinokitiol, and resorcin.

Examples of the pH adjusting agent used include sodium hydroxide, triethanolamine, citric acid, sodium citrate, boric acid, borax, and potassium hydrogen phosphate.

Examples of the antioxidant used include dibutylhydroxytoluene, butylhydroxyanisole, propyl gallate, and ascorbic acid.

Examples of the UV filter used include p-aminobenzoic acid UV absorbers, anthranilic acid UV absorbers, salicylic acid UV absorbers, cinnamic acid UV absorbers, benzophenone UV absorbers, sugar UV absorbers, 3-(4-methylbenzylidene)-d-camphor, 3-benzylidene-d,l-camphor, urocanic acid, ethyl urocanate ester, 2-phenyl-5-methylbenzoxazole, 2,2-hydroxy-5-methylphenylbenzotriazole, 2-(2-hydroxy-5-t-octylphenyl)benzotriazole, 2-(2-hydroxy-5-methylphenyl) benzotriazole, dibenzalazine, dianisoylmethane, 4-methoxy-4-t-butyl benzoyl methane, 5-(3,3-dimethyl-2-norbornylidene)-3-pentan-2-one, 2-hydroxy-4-methoxybenzophenone, octyldimethyl p-aminobenzoate, ethylhexyl p-methoxy cinnamate, titanium oxide fine particles, and zinc oxide fine particles.

Examples of the pigment used include silica, mica, talc, sericite, barium sulfate, titanium dioxide, chromium oxide, iron oxide, zinc oxide, cerium dioxide, zirconium dioxide, carbon black, barium, strontium, nylon powder, and polymethyl methacrylate (PMMA).

Examples of the antiseptic used include parabens such as methyl paraben and propyl paraben, phenoxyethanol, octanediol, and hexanediol.

With regard to the optional components as described above, a water-soluble component is preferably added to the aqueous phase, and oil phase component is preferably added to the silicone oil phase.

The method for producing the water-in-silicone oil macroemulsion of the present invention is not particularly limited, and any method used for emulsification in the art may be used for the production.

More specifically, the method for producing the water-in-silicone oil macroemulsion of the present invention comprises the steps of S1) mixing a partly crosslinked emulsifiable silicone elastomer, a partly crosslinked non-emulsifiable silicone elastomer, and a non-crosslinked silicone emulsifier with a silicone oil to produce the silicone oil phase, S2) mixing 1,3-butylene glycol and a lower alcohol, and also, at least one member selected from the group consisting of organic acid salts, inorganic salts, and polyhydric alcohols other than glycerin and 1,3-butylene glycol with water to produce the aqueous phase, and S3) adding the aqueous phase part (W) to the silicone oil phase part to produce the water-in-silicone oil (W/S) macroemulsion.

In this case, the ratio of the silicone oil phase part (S) to the aqueous phase part is adequately selected. The weight ratio of the silicone oil phase part: the aqueous phase part is preferably 7:93 to 40:60 in view of simultaneously satisfying the requirements for the stability of the cosmetic composition and good feeling during the use.

Excessively high proportion of the silicone oil phase part may result in the loss of waterly feel in the use of the cosmetic composition while excessively high proportion of the aqueous phase part may result in the loss of the stability of the cosmetic composition.

Next, the production method is described in detail step by step.

First, the silicone oil component, the crosslinked emulsifiable silicone elastomer, the partly crosslinked non-emulsifiable silicone elastomer, and the non-crosslinked silicone emulsifier are mixed to prepare the silicone oil phase part (S). (S1)

The production of the silicone oil phase part may be conducted by the method commonly used in the art in an agitatable and temperature-regulatable vacuum emulsification tank with optional agitationa and heating to homogeneously mix other components in the silicone oil.

If necessary, an oil-soluble physiologically active component may also be added in this stage, and exemplary oil-soluble physiologically active components used include any of those known in the field, for example, active component having wrinkle improving effects such as retinol and derivatives thereof (for example, retinol palmitate), adenosine, and the like.

Next, 1,3-butylene glycol and a lower alcohol, and also, an organic acid salt, an inorganic salt, and glycerin, and at least one member selected from the group consisting of polyhydric alcohols other than glycerin and 1,3-butylene are added to the water to thereby produce the aqueous phase part (W).

As in the case of production of the silicone oil phase part, the production of the aqueous phase part (W) may be conducted by the method commonly used in the art in an agitatable and temperature-regulatable vacuum emulsification tank with optional agitation and heating to homogeneously mix other components in the water.

If necessary, a water-soluble physiologically active component may also added in this stage, and exemplary water-soluble physiologically active components used include any of those known in the field, for example, active component having whitening effects such as oil-soluble licorice, ethylascorbyl ether, α-bisabolol, and the like.

Next, the aqueous phase part as described above is added to the silicone oil phase part to produce the water-in-silicone oil (W/S) macroemulsion. (S3)

The water-in-silicone oil macroemulsion may be produced in a vacuum emulsifying tank by agitating the mixture with a dispersion mixer at a speed of 1,000 to 3,000 rpm, and preferably 1,200 to 2,500 rpm for 1 to 10 minutes.

The thus produced water-in-silicone oil macroemulsion is preferably produced in the form of an emulsion having a particle size larger than the ordinary emulsion particles, namely, a particle size with the average size of 5 to 20 μm. The water-in-silicone oil macroemulsion having the particle size of such range is produced in the particle size larger than the conventional fine emulsion particles, and when brought in contact with the skin or a pressure is applied, breakage of the emulsion instantaneously results in the release of water content (namely, the aqueous phase portion) with the relative increase in the contact area with the skin, and hence, increase in the percutaneous absorption and percutaneous absorption area.

More specifically, the water-in-silicone oil macroemulsion of the present invention can retain stable dispersion phase at a high temperature, room temperature, and low temperature, and the retention of the stable dispersion phase was confirmed after repeated freezing and thawing at −20° C. and room temperature.

Such water-in-silicone oil macroemulsion can be used in various cosmetic composition of various dosage form including solution, suspension, milky lotion, paste, gel, cream, lotion, powder, cleansing cream, oil, foundation, spray, and the like.

For example, the water-in-silicone oil macroemulsion composition may be used as a composition of basic cosmetics selected from moisturizer, nutrient lotion, lotion, cream, pack, gel, patch, and spray (mist) as well as composition of color tone cosmetics selected from lip stick, make up base, and foundation.

The composition of each dosage form may contain various matrix and additives required and adequate for the production of the preparation of the dosage form, and the composition may known compounds such as nonionic surfactant, silicone polymer, extender, flavor, antiseptic, bactericide, oxidation stabilizer, organic solvent, ionic or nonionic thickener, softener, antioxidant, free radical breaker, opacification agent, stabilizer, emollient, silicone, α-hydroxy acid, antifoaming agent, humectant, vitamin, insect repellent, flavor, preservative, surfactant, antiphlogistic, substance P antagonist, filler, polymer, propellant, basification or acidification agent, or colorant to the extent not adversely affecting the merits of the composition.

EXAMPLES

Next, the present invention is described in further detail by referring to Examples which by no means limit scope of the invention since various alteration and modification can be made on the present invention. The Examples of the present invention are provided to more fully explain the present invention to those skilled in the art.

Examples and Comparative Examples

Production of Emulsion Compositions

Water-in-silicone oil macroemulsion compositions having the composition as shown in the following Tables 1 to 6 were produced.

First, the constituents of the silicone oil phase part were introduced in a vessel, and the mixture was agitated in a dispersion mixer at 1,000 rpm for 3 minutes to prepare the homogeneous oil phase part mixture. Next, the constituents of the aqueous phase part were introduced in a vessel, and the mixture was agitated in a dispersion mixer at 1,000 rpm for 3 minutes to prepare the aqueous phase part. This aqueous phase part was added to the silicone oil phase part, and the mixture was agitated at 1,500 rpm for 5 minutes to produce a water-in-silicone oil (W/S) macroemulsion composition.

The partly crosslinked emulsifiable silicone elastomer ("emulsifiable elastomer") used was a mixture of dimethicone/PEG-10/15 crosspolymer and dimethicone (manufactured by Shin-Etsu Chemical Co., Ltd., KSG-210), the partly crosslinked non-emulsifiable silicone elastomer ("non-emulsifiable elastomer") was a mixture of dimethicone/vinyl dimethicone crosspolymer and cyclopentasiloxane (manufactured by Shin-Etsu Chemical Co., Ltd., KSG-15), the non-crosslinked silicone emulsifier was PEG-10 dimethicone (manufactured by Shin-Etsu Chemical Co., Ltd., KF-6017), and the silicone oil was dimethicone.

TABLE 1

| Composition (% by weight) | | Example | | | | |
|---|---|---|---|---|---|---|
| | | 1 | 2 | 3 | 4 | 5 |
| Oil phase part | Emulsifiable elastomer | 3.0 | 3.0 | 3.0 | 3.0 | 3.0 |
| | Non-emulsifiable elastomer | 1.0 | 1.0 | 1.0 | 1.0 | 1.0 |
| | Silicone emulsifier | 0.1 | 0.1 | 0.1 | 0.2 | 0.1 |
| | Silicone oil | 8.9 | 8.9 | 8.9 | 8.9 | 8.9 |
| Aqueous phase part | 1,3-butylene glycol | 8.0 | 8.0 | 8.0 | 8.0 | 8.0 |
| | Ethanol | 10.0 | 5.0 | 5.0 | 10.0 | 5.0 |
| | Sodium citrate | 0.2 | 0.2 | 0.2 | 0.2 | 0.2 |
| | Sodium chloride | 0.5 | 1.0 | — | 0.5 | — |
| | Magnesium sulfate | — | — | 0.2 | — | 0.4 |
| | Ethylene glycol | — | — | — | 0.5 | — |
| | Polyethylene glycol | — | — | — | — | — |
| | Sorbitol | — | — | — | — | — |
| | Glucose | — | — | — | — | — |
| | Purified water | Remainder | Remainder | Remainder | Remainder | Remainder |
| Total | | 100 | 100 | 100 | 100 | 100 |

TABLE 2

| Composition (% by weight) | | Example | | | |
|---|---|---|---|---|---|
| | | 6 | 7 | 8 | 9 |
| Oil phase part | Emulsifiable elastomer | 3.0 | 3.0 | 3.0 | 3.0 |
| | Non-emulsifiable elastomer | 1.0 | 1.0 | 1.0 | 1.0 |
| | Silicone emulsifier | 0.1 | 0.1 | 0.1 | 0.1 |
| | Silicone oil | 8.9 | 8.9 | 8.9 | 8.9 |
| Aqueous phase part | 1,3-butylene glycol | 8.0 | 8.0 | 8.0 | 8.0 |
| | Ethanol | 10.0 | 5.0 | 5.0 | 5.0 |
| | Sodium citrate | 0.2 | 0.2 | 0.2 | 0.2 |
| | Sodium chloride | 0.5 | 0.5 | 0.5 | 0.5 |
| | Magnesium sulfate | — | — | — | — |
| | Ethylene glycol | — | — | — | 0.1 |
| | Polyethylene glycol | 0.5 | — | — | 0.2 |
| | Sorbitol | — | 2.0 | — | 0.1 |
| | Glucose | — | — | 0.5 | 0.1 |
| | Purified water | Remainder | Remainder | Remainder | Remainder |
| Total | | 100 | 100 | 100 | 100 |

TABLE 3

| Composition (% by weight) | | Comparative Example | | | | |
|---|---|---|---|---|---|---|
| | | 1 | 2 | 3 | 4 | 5 |
| Oil phase part | Emulsifiable elastomer | 3.0 | 3.0 | 3.0 | 3.0 | 3.0 |
| | Non-emulsifiable elastomer | 1.0 | 1.0 | 1.0 | 1.0 | 1.0 |
| | Silicone emulsifier | 0.2 | 0.1 | 0.1 | 0.1 | 0.1 |
| | Silicone oil | 8.9 | 8.9 | 8.9 | 8.9 | 8.9 |

TABLE 3-continued

| Composition (% by weight) | | Comparative Example | | | | |
|---|---|---|---|---|---|---|
| | | 1 | 2 | 3 | 4 | 5 |
| Aqueous phase part | 1,3-butylene glycol | 15.0 | — | — | — | — |
| | Ethanol | — | 15.0 | — | — | — |
| | Sodium citrate | — | — | 1.0 | — | — |
| | Sodium chloride | — | — | — | 2.5 | — |
| | Magnesium sulfate | — | — | — | — | — |
| | Ethylene glycol | — | — | — | — | — |
| | Polyethylene glycol | — | — | — | — | 2.0 |
| | Sorbitol | — | — | — | — | — |
| | Glucose | — | — | — | — | — |
| | Purified water | Remainder | Remainder | Remainder | Remainder | Remainder |
| | Total | 100 | 100 | 100 | 100 | 100 |

TABLE 4

| Composition (% by weight) | | Comparative Example | | | | |
|---|---|---|---|---|---|---|
| | | 6 | 7 | 8 | 9 | 10 |
| Oil phase part | Emulsifiable elastomer | 3.0 | 3.0 | 3.0 | 3.0 | 3.0 |
| | Non-emulsifiable elastomer | 1.0 | 1.0 | 1.0 | 1.0 | 1.0 |
| | Silicone emulsifier | 0.2 | 0.1 | 0.1 | 0.2 | 0.1 |
| | Silicone oil | 8.9 | 8.9 | 8.9 | 8.9 | 8.9 |
| Aqueous phase part | 1,3-butylene glycol | — | 13.0 | 8.0 | 5.0 | 21.0 |
| | Ethanol | 13.0 | — | 5.0 | 5.0 | 5.0 |
| | Sodium citrate | 0.2 | 0.2 | — | 0.2 | 0.2 |
| | Sodium chloride | 0.5 | 0.5 | — | 0.5 | 0.5 |
| | Magnesium sulfate | — | — | — | — | — |
| | Ethylene glycol | — | — | — | — | — |
| | Polyethylene glycol | — | — | — | — | — |
| | Sorbitol | — | — | — | — | — |
| | Glucose | — | — | — | — | — |
| | Purified water | Remainder | Remainder | Remainder | Remainder | Remainder |
| | Total | 100 | 100 | 100 | 100 | 100 |

TABLE 5

| Composition (% by weight) | | Comparative Example | | | | |
|---|---|---|---|---|---|---|
| | | 11 | 12 | 13 | 14 | 15 |
| Oil phase part | Emulsifiable elastomer | 3.0 | 3.0 | 3.0 | 3.0 | 3.0 |
| | Non-emulsifiable elastomer | 1.0 | 1.0 | 1.0 | 1.0 | 1.0 |
| | Silicone emulsifier | 0.1 | 0.1 | 0.1 | 0.2 | 0.1 |
| | Silicone oil | 8.9 | 8.9 | 8.9 | 8.9 | 8.9 |
| Aqueous phase part | 1,3-butylene glycol | 8.0 | 8.0 | 8.0 | — | 13.0 |
| | Ethanol | 4.0 | 20.0 | 5.0 | 13.0 | — |
| | Sodium citrate | 0.2 | 0.2 | 0.1 | 0.1 | 0.2 |
| | Sodium chloride | 0.5 | 0.5 | 0.2 | 3.0 | 0.5 |
| | Magnesium sulfate | — | — | — | — | — |
| | Ethylene glycol | — | — | — | — | 4.0 |
| | Polyethylene glycol | — | — | — | — | — |
| | Sorbitol | — | — | — | — | — |
| | Glucose | — | — | — | — | — |
| | Purified water | Remainder | Remainder | Remainder | Remainder | Remainder |
| | Total | 100 | 100 | 100 | 100 | 100 |

TABLE 6

| Composition | | Comparative Example | | |
|---|---|---|---|---|
| (% by weight) | | 16 | 17 | 18 |
| Oil phase part | Emulsifiable elastomer | 3.0 | 3.0 | 3.0 |
| | Non-emulsifiable elastomer | 1.0 | 1.0 | 1.0 |
| | Silicone emulsifier | 0.1 | 0.1 | 0.1 |
| | Silicone oil | 8.9 | 8.9 | 8.9 |
| Aqueous phase part | 1,3-butylene glycol | 8.0 | 8.0 | 8.0 |
| | Ethanol | 5.0 | 5.0 | 5.0 |
| | Sodium citrate | 0.2 | 0.2 | 0.2 |
| | Sodium chloride | 0.5 | 0.5 | 0.5 |
| | Magnesium sulfate | — | — | — |
| | Ethylene glycol | — | — | — |
| | Polyethylene glycol | 4.0 | — | — |
| | Sorbitol | — | 4.0 | — |
| | Glucose | — | — | 4.0 |
| | Purified water | Remainder | Remainder | Remainder |
| | Total | 100 | 100 | 100 |

Test Example 1

Particles Size and Distribution State

In order to confirm the particles of the water-in-silicone oil macroemulsion produced in Example 2, measurement was conducted by using an optical microscope. The results are shown in FIG. 1. Based on FIG. 1, the water-in-silicone oil macroemulsion of Example 2 was found to have a particle size in the level of 5 to 20 μm.

In order to confirm the dispersion state of the water-in-silicone oil macroemulsions produced in Examples 1, 2, 3, 4, 6, 7, and 8, measurement was conducted by using an optical microscope. The results are shown in FIGS. 2(a) to 2(g). FIGS. 2(a) to 2(g) are respectively pictures taken by the optical microscope of the water-in-silicone oil macroemulsion of Examples 1, 2, 3, 4, 6, 7, and 8, and stable dispersion of these macroemulsions were thereby confirmed.

Test Example 2

Evaluation of the Stability

In order to confirm the stability of the water-in-silicone oil macroemulsion compositions produced in the Examples and Comparative Examples, the stability was evaluated by leaving the macroemulsion composition in a thermostatic tank and circulation tank. The stability was evaluated in the conditions as shown below.

TABLE 7

| Evaluation | Method |
|---|---|
| High temperature stability | Evaluated after storing in a thermostatic chamber at 45° C. for 3 months |
| Room temperature stability | Evaluated after storing in a thermostatic chamber at 25° C. for 3 months |
| Low temperature stability | Evaluated after storing in a thermostatic chamber at 5° C. for 3 months |
| Circulation stability | Evaluated after storing in a circulating tank for 3 month 0° C. (6 hr) → 15° C. (6 hr) → 30° C. (6 hr) → 45° C. (6 hr) → 30° C. (6 hr) → 15° C. (6 hr) → 0° C. (6 hr) |

TABLE 7-continued

| Evaluation | Method |
|---|---|
| Freeze-thaw stability | 3 cycles of storing at −20° C. for 2 weeks and storing at room temperature for 2 days |
| Evaluation | A: excellent |
| | B: good |
| | C: slight inconvenience but not practically unacceptable |
| | D: poor (discoloration, odor, separation) |

TABLE 8

| | | High temperature stability | Room temperature stability | Low temperature stability | Circulation stability | Freeze-thaw stability |
|---|---|---|---|---|---|---|
| Example | 1 | A | A | A | A | A |
| | 2 | A | A | A | A | A |
| | 3 | A | A | A | A | A |
| | 4 | A | A | A | A | A |
| | 5 | A | A | A | A | A |
| | 6 | A | A | A | A | A |
| | 7 | A | A | A | A | A |
| | 8 | A | A | A | A | A |
| | 9 | A | A | A | A | A |
| Comparative Example | 1 | C | C | C | C | C |
| | 2 | D | D | D | D | D |
| | 3 | C | C | D | D | D |
| | 4 | C | C | C | C | D |
| | 5 | C | D | D | D | D |
| | 6 | C | C | C | C | D |
| | 7 | B | B | C | C | D |
| | 8 | D | D | D | D | D |
| | 9 | B | B | B | B | D |
| | 10 | C | C | C | C | B |
| | 11 | B | B | B | B | D |
| | 12 | D | D | D | D | D |
| | 13 | C | C | C | C | D |
| | 14 | D | D | D | D | D |
| | 15 | B | B | B | C | B |
| | 16 | B | B | B | C | B |
| | 17 | B | B | B | C | B |
| | 18 | B | B | B | C | B |

As demonstrated in Table 8, all cosmetic compositions of the Examples exhibited excellent high temperature, room temperature, low temperature, circulation, and freeze-thaw stabilities. In contrast, all cosmetic compositions of the Comparative Examples were inferior in the stability in the repeated freezing and thawing.

Test Example 3

Sensory Test

The water-in-silicone oil (W/S) macroemulsions produced in the Examples and Comparative Examples were evaluated for their waterdrop quick break effect, moist feeling, spreadability, and adhesion in a test by 20 women at 20 to 40 years old. The results are showing Table 9, below. The evaluation was conducted by the following criteria.

Poor: D

Relatively poor: C

Acceptable: B

Excellent: A

TABLE 9

| | | Waterdrop quick break effect | Moist feel | Spreadability | Adhesion |
|---|---|---|---|---|---|
| Example | 1 | A | A | A | A |
| | 2 | A | A | A | A |
| | 3 | A | A | A | A |
| | 4 | A | A | A | A |
| | 5 | A | A | A | A |
| | 6 | A | A | A | A |
| | 7 | A | A | A | A |
| | 8 | A | A | A | A |
| | 9 | A | A | A | A |
| Comparative Example | 1 | A | A | A | A |
| | 2 | A | D | A | C |
| | 3 | A | D | A | C |
| | 4 | A | D | A | C |
| | 5 | A | C | A | C |
| | 6 | A | D | A | C |
| | 7 | A | A | A | A |
| | 8 | A | A | A | A |
| | 9 | A | B | A | A |
| | 10 | A | B | D | B |
| | 11 | A | A | A | A |
| | 12 | A | D | A | A |
| | 13 | A | A | A | A |
| | 14 | A | D | A | C |
| | 15 | A | A | D | A |
| | 16 | A | A | D | A |
| | 17 | A | A | D | A |
| | 18 | A | A | D | A |

As demonstrated in Table 9, the user could feel waterdrop quick break effect of the composition of the Examples without feeling sacrifice of the spreadability, adhesion, and retention.

Japanese Patent Application No. 2012-249315 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A water-in-silicone oil macroemulsion cosmetic composition comprising a silicone oil phase part and aqueous phase, wherein
the silicone oil phase part (S) comprises a partly crosslinked emulsifiable silicone elastomer, a partly crosslinked non-emulsifiable silicone elastomer, a non-crosslinked silicone emulsifier, and a silicone oil, and
the aqueous phase part is substantially free from glycerin, and the aqueous phase part (W) contains 1,3-butylene glycol and a lower alcohol at a total amount of 13 to 18% by weight of the entire composition, and at least one member selected from the group consisting of organic acid salts, inorganic salts, and polyhydric alcohols other than glycerin and 1,3-butylene glycol at a total amount of 0.4 to 3.0% by weight of the entire composition as a freeze stabilizer,
wherein the weight ratio of the silicone oil phase part (S): the aqueous phase part being 7:93 to 13.1:86.9 and water content being 67.7 to 73.6% by weight in the composition, and
wherein the water-in-silicone oil macroemulsion is in the form of an emulsion having an average particle size of 5 to 20 μm.

2. A water-in-silicone oil macroemulsion cosmetic composition of claim 1 wherein the 1,3-butylene glycol and the lower alcohol is 4:1 to 1:2 in the weight ratio.

3. A water-in-silicone oil macroemulsion cosmetic composition of claim 1 wherein the content of the organic acid salt is present in an amount of 0.05 to 0.5% by weight of the entire composition.

4. A water-in-silicone oil macroemulsion cosmetic composition according to claim 1 wherein the lower alcohol is at least one member selected from methanol, ethanol, isopropanol, butanol, and pentanol.

5. A water-in-silicone oil macroemulsion cosmetic composition according to claim 1 wherein the organic acid salt is at least one member selected from the group consisting of sodium citrate, sodium formate, sodium acetate, and potassium acetate.

6. A water-in-silicone oil macroemulsion cosmetic composition according to claim 1 wherein the inorganic salt is at least one member selected from sodium chloride, potassium chloride, calcium chloride, magnesium chloride, and magnesium sulfate.

7. A water-in-silicone oil macroemulsion cosmetic composition according to claim 6 wherein the inorganic salt is at least one member selected from sodium chloride and potassium chloride.

8. A water-in-silicone oil macroemulsion cosmetic composition according to claim 1 wherein the polyhydric alcohol is least one member selected from ethylene glycol, propylene glycol, dipropylene glycol, tripropylene glycol, diethylene glycol, sorbitol, mannitol, maltitol, lactitol, glucose, polyethylene glycol, and polypropylene glycol.

9. A water-in-silicone oil macroemulsion cosmetic composition according to claim 1, wherein the non-crosslinked silicone emulsifier is incorporated at an amount of from 0.03% by weight in relation to the total weight of silicone oil phase to 0.2% by weight in relation to the weight of the entire composition, the aqueous phase part is free from glycerin, and the aqueous phase part (W) contains 1,3-butylene glycol and a lower alcohol selected from methanol, ethanol, isopropanol, butanol, and pentanol at a total amount of 13 to 18% by weight of the entire composition, and at least one member selected from the group consisting of organic acid salts, inorganic salts, and polyhydric alcohols other than glycerin and 1,3-butylene glycol at a total amount of 0.4 to 3.0% by weight of the entire composition as a freeze stabilizer part.

* * * * *